(12) United States Patent
Keller et al.

(10) Patent No.: US 9,439,711 B2
(45) Date of Patent: Sep. 13, 2016

(54) MEDICAL DEVICES FOR THERMALLY TREATING TISSUE

(71) Applicant: COVIDIEN LP, Mansfield, MA (US)

(72) Inventors: Craig A. Keller, Boulder, CO (US); Robert B. Smith, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 195 days.

(21) Appl. No.: 14/029,893

(22) Filed: Sep. 18, 2013

(65) Prior Publication Data

US 2014/0094786 A1     Apr. 3, 2014

Related U.S. Application Data

(60) Provisional application No. 61/708,840, filed on Oct. 2, 2012, provisional application No. 61/809,061, filed on Apr. 5, 2013.

(51) Int. Cl.
| | |
|---|---|
| A61B 18/04 | (2006.01) |
| A61B 18/08 | (2006.01) |
| A61B 18/10 | (2006.01) |
| A61B 18/14 | (2006.01) |
| A61B 18/00 | (2006.01) |
| A61B 18/12 | (2006.01) |

(52) U.S. Cl.
CPC ............. *A61B 18/085* (2013.01); *A61B 18/10* (2013.01); *A61B 18/1445* (2013.01); *A61B 2018/0063* (2013.01); *A61B 2018/00095* (2013.01); *A61B 2018/00101* (2013.01); *A61B 2018/00642* (2013.01); *A61B 2018/00791* (2013.01); *A61B 2018/1226* (2013.01); *A61B 2018/1495* (2013.01)

(58) Field of Classification Search
CPC . A61B 18/085; A61B 18/10; A61B 18/1445
USPC ...................................... 606/51–52
See application file for complete search history.

(56) References Cited

U.S. PATENT DOCUMENTS

| | | |
|---|---|---|
| D249,549 S | 9/1978 | Pike |
| 4,219,025 A * | 8/1980 | Johnson ............... A61B 18/082 219/233 |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

U.S. Appl. No. 08/926,869, filed Sep. 10, 1997, James G. Chandler.

(Continued)

*Primary Examiner* — Daniel Fowler

(57) ABSTRACT

A medical device for treating tissue includes a tissue-contacting surface and a solid state heating element that is thermally coupled to the tissue-contacting surface. The solid state heating element is configured to generate heat to thermally treat tissue.

4 Claims, 5 Drawing Sheets

(56) References Cited

U.S. PATENT DOCUMENTS

| | | |
|---|---|---|
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| 5,980,518 A * | 11/1999 | Carr et al. ............... 606/45 |
| D424,694 S | 5/2000 | Tetzlaff et al. |
| D425,201 S | 5/2000 | Tetzlaff et al. |
| 6,083,223 A * | 7/2000 | Baker ................... 606/52 |
| H1904 H | 10/2000 | Yates et al. |
| 6,249,706 B1 | 6/2001 | Sobota et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,908,463 B2 | 6/2005 | Treat et al. |
| 6,926,716 B2 | 8/2005 | Baker et al. |
| 6,929,644 B2 | 8/2005 | Truckai et al. |
| D509,297 S | 9/2005 | Wells |
| 6,994,709 B2 | 2/2006 | Iida |
| 7,025,763 B2 | 4/2006 | Karasawa et al. |
| D525,361 S | 7/2006 | Hushka |
| 7,108,694 B2 | 9/2006 | Miura et al. |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| 7,326,202 B2 | 2/2008 | McGaffigan |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 8,128,624 B2 | 3/2012 | Couture et al. |
| 8,142,425 B2 | 3/2012 | Eggers |
| D661,394 S | 6/2012 | Romero et al. |
| 8,197,472 B2 | 6/2012 | Lau et al. |
| 2001/0018601 A1* | 8/2001 | Ingle et al. ............... 607/96 |
| 2003/0139742 A1 | 7/2003 | Wampler et al. |
| 2003/0236518 A1 | 12/2003 | Marchitto et al. |
| 2004/0078035 A1 | 4/2004 | Kanehira et al. |
| 2004/0243125 A1* | 12/2004 | Dycus et al. ............ 606/51 |
| 2010/0185197 A1 | 7/2010 | Sakao et al. |
| 2010/0228250 A1* | 9/2010 | Brogna ................... 606/45 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |

(56) References Cited

FOREIGN PATENT DOCUMENTS

| WO | 0115614 A1 | 3/2001 |
|---|---|---|
| WO | 0154604 A1 | 8/2001 |
| WO | 02045589 A3 | 9/2002 |
| WO | 2006/021269 A1 | 3/2006 |
| WO | 2005110264 A3 | 4/2006 |
| WO | 2008/040483 A1 | 4/2008 |
| WO | 2011/018154 A1 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/868,732, filed Apr. 23, 2013, Mueller.
U.S. Appl. No. 13/893,527, filed May 14, 2013, Horner.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 4, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.
U.S. Appl. No. 13/969,278, filed Aug. 16, 2013, Kerr.
U.S. Appl. No. 14/017,572, filed Sep. 4, 2013, Arya.
U.S. Appl. No. 14/019,031, filed Sep. 5, 2013, Garrison.
U.S. Appl. No. 14/019,094, filed Sep. 5, 2013, Garrison.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, No. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.

(56) References Cited

OTHER PUBLICATIONS

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

\* cited by examiner

MEDICAL DEVICES FOR THERMALLY TREATING TISSUE

CROSS-REFERENCE TO RELATED APPLICATIONS

This application claims the benefit of, and priority to, U.S. Provisional Patent Application No. 61/708,840, filed on Oct. 2, 2012, and U.S. Provisional Patent Application No. 61/809,061, filed on Apr. 5, 2013, the entire contents of each of which are hereby incorporated by reference herein.

BACKGROUND

1. Technical Field

The present disclosure relates to medical devices and, more particularly, to medical devices capable of heating tissue to thermally treat tissue.

2. Background of Related Art

Energy-based medical devices are typically used in conjunction with energy sources (external energy sources or portable energy sources incorporated into the instruments themselves) to apply and control the application of energy to tissue to thermally treat, e.g., heat, tissue to achieve a desired tissue effect. Energy-based surgical forceps, for example, utilize both the mechanical clamping action of the jaw members and the energy provided by the energy source and delivered to tissue to heat tissue grasped between the jaw members to achieve a desired tissue effect, e.g., to seal tissue. Various forms of energy, e.g., RF energy, ultrasonic energy, microwave energy, thermal energy, light energy, etc., may be employed to heat tissue to achieve a desired tissue effect.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any of the other aspects described herein.

A medical device for treating tissue provided in accordance with aspects of the present disclosure includes a tissue-contacting surface and a solid state heating element thermally coupled to the tissue-contacting surface. The solid state heating element is configured to generate heat to thermally treat tissue.

In aspects, the medical device further includes control circuitry coupled to the solid state heating element. The control circuitry is configured to regulate heat generation by the solid state heating element In aspects, the control circuitry and the solid state heating element are packaged or integrated together. More specifically, the control circuitry and the solid state heating element may be part of an integrated circuit.

In aspects, the medical device further includes one or more temperature-sensing elements. The one or more temperature-sensing elements are configured to sense a temperature of the solid state heating element, tissue, and/or another element thermally coupled to the solid state heating element or tissue.

In aspects, the temperature-sensing element and the solid state heating element are packaged or integrated together. More specifically, the temperature-sensing element and the solid state heating element may be part of an integrated circuit.

In aspects, the temperature-sensing element is coupled to the control circuitry for feedback-based control of the solid state heating element. More specifically, the feedback-based control may be provided to limit the temperature of the solid state heating element.

In aspects, the medical device further includes a power source coupled to the solid state heating element. The power source is configured to supply energy to the solid state heating element.

In aspects, the power source is integrated or packaged with the solid state heating element. The power source may be a battery.

In aspects, the solid state heating element includes one or more transistors configured to generate heat to thermally treat tissue.

Another medical device for treating tissue provided in accordance with the present disclosure includes an end effector assembly having first and second jaw members. One or both of the jaw members is movable relative to the other between a spaced-apart position and an approximated position for grasping tissue therebetween. Each of the jaw members includes a tissue-contacting surface. A solid state heating element is thermally coupled to one or both of the tissue-contacting surfaces. The solid state heating element is configured to generate heat to thermally treat tissue.

In aspects, the medical device further includes control circuitry coupled to the solid state heating element. The control circuitry is configured to regulate heat generation by the solid state heating element.

In aspects, the control circuitry and the solid state heating element are packaged or integrated together.

In aspects, the medical device further includes one or more temperature-sensing elements. The one or more temperature-sensing elements are configured to sense a temperature of the solid state heating element, tissue, and/or another element thermally coupled to the solid state heating element or tissue.

In aspects, the temperature-sensing element is coupled to the control circuitry for feedback-based control of the solid state heating element.

In aspects, the solid state heating element is disposed within one of the jaw members and the temperature-sensing element is disposed within the other of the jaw members.

In aspects, the medical device further includes a power source coupled to the solid state heating element and configured to supply energy to the solid state heating element.

In aspects, the solid state heating element includes one or more transistors configured to generate heat to thermally treat tissue.

BRIEF DESCRIPTION OF THE DRAWINGS

Various aspects of the present disclosure are described herein with reference to the drawings wherein like reference numerals identify similar or identical elements.

DETAILED DESCRIPTION

Figure 4:
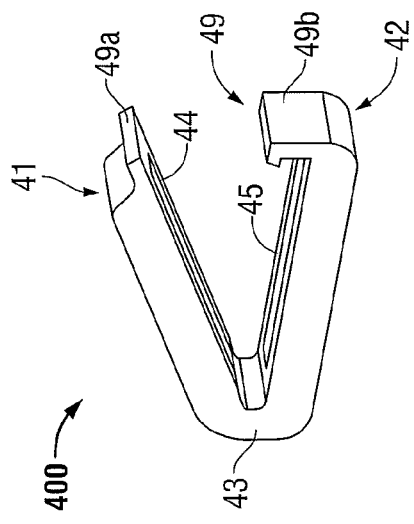
FIG. 4 is a front, perspective view of a surgical tissue clip configured for use in accordance with the present disclosure.

There are a wide variety of medical devices that effect the heating of tissue to treat tissue. Tissue heating can be accomplished by Joule heating, e.g., passing current through tissue; conductive heating, e.g., placing a heated surface in contact with or in close proximity to tissue; dielectric heating, e.g., applying a changing electric field to tissue; and/or frictional heating, e.g., creating friction within tissue. With respect to conductive heating of tissue, some of the challenges include achieving high power densities, a low thermal mass, a manufacturable package, temperature-sensing that is thermally linked with the heating elements, and temperature control.

The present disclosure provides for the use of solid state devices, e.g., transistors and other heat generating components of solid state devices, as a source of heat for conductively heating tissue to thermally treat tissue. Such solid state heating systems can be incorporated into any suitable medical device configured to treat tissue. For example, a solid state heating system of the present disclosure may be incorporated into: one or both jaw members of a surgical forceps configured to grasp tissue between its jaw members and heat tissue to seal tissue; an ablation probe used to internally heat tumors or other tissue to destroy the tumors or other tissue; or on a surface of a medical device configured to be placed over, around, or about tissue for warming the tissue to provide relief and/or promote healing. Accordingly, since the present disclosure is not limited to a particular instrument and/or configuration, the present disclosure will be described initially in a more general respect, followed by a more specific description of exemplary configurations.

The solid state heating systems of the present disclosure may incorporate one or more solid state devices which include, for example, transistors, microprocessors, RAM, semiconductor diodes, integrated circuits (IC's), etc. Each of these components may themselves include any suitable type of transistor(s) (e.g., bipolar junction, field-effect, etc.), and/or other solid state heating components (e.g., resistive elements). The transistors may be configured to operate in various modes (e.g., switching or active) to generate heat for treating tissue. More specifically, heat generation by the transistors may be controlled by changing the operating point of one or more of the transistors (where the transistors are operating in an active mode), or by changing the switching frequency of one or more of the transistors (where the transistors are operating in a switching mode). This and other control functionality may be provided via analog circuitry, digital logic circuitry, and/or software operating on a microcontroller, the same or another solid state device, or a separate control device or system. Transistors based on different materials (e.g., Si, GaAs, SiC, etc.) may also be provided, depending on a particular purpose, e.g., operating temperature limitations, voltage limits, operating mode, and/or power handling capability. Resistive elements within the solid state devices may also be specifically provided for generating heat via resistive loss, and may likewise be made from different materials (e.g., Si or other suitable metallic materials) depending on a particular purpose. Further, the solid state devices may be operated at relatively high voltages to allow power to be transmitted at relatively smaller currents and to reduce transmission losses.

The solid state heating systems of the present disclosure may include control circuitry, one or more temperature sensitive elements coupled to the control circuitry, and transistors (coupled to or integrated with the control circuitry) that are utilized to generate heat for heating tissue. By monitoring the temperature sensitive element, the control circuitry can control the transistors, thereby controlling heat generation to achieve any desired trace of temperature versus time at the location of the temperature sensor. Because solid state devices can be very small, it is possible to achieve tight thermal coupling of the transistors, the temperature monitoring element, and the target tissue to thereby enable rapid and accurate thermal dosing of the target tissue. Thus, monitoring of the temperature sensitive element effectively becomes monitoring of the temperature of the target tissue and of the transistors.

The solid state heating systems of the present disclosure may be formed from one or more solid state devices packaged individually and/or packaged together in one or more sets. Multiple packages of a system may be provided together on a substrate, may be coupled to one another, or may be remote from one another. In some embodiments, the package(s) themselves function as a tissue-contacting surface to facilitate the heating and thermal treatment of tissue using the heat generated by the transistors (or other components) of the solid state devices. The packages may further include control circuitry and/or sensor circuitry integrated therewith. The package(s) may be configured to define any suitable configuration, e.g., linear, curved, etc., depending on a particular purpose. Trapezoidal-shaped packages, for example, allow adjacent packages to be fit together in either a linear or curved configuration (depending on their orientation), with minimal spacing between adjacent packages, to define a suitable tissue-contacting surface. However, other suitably shaped packages are also contemplated. In embodiments where the package(s) form a tissue-contacting surface, the packages may further include specific features to facilitate tissue treatment, e.g., textured surfaces or projections to facilitate grasping tissue, stop features to inhibit contact between surfaces and/or define a gap distance therebetween, etc., and may additionally or alternatively be etched, cut, grinded, coated with a textured material, film, etc. to provide a particular surface feature such as, for example, anti-stick characteristics.

The solid state heating systems of the present disclosure may be coupled to a separate control system, e.g., a control system that is not integrated into the heat-generating system. Alternatively, the solid state heating system may include one or more solid state devices configured for heat-generation and one or more solid state devices configured for control. The one or more heating generating devices and one or more control devices may comprise the same solid state device, may be separate solid state devices integrated into a single package, or may be separate packages (or standalone devices) of the system. Power may be provided to the solid state heating system, for example, via a battery (either integrated into the system or separate therefrom), or other power supply.

Transistors of the solid state heating systems of the present disclosure may be provided in one or more groups and/or solid state devices, with multiple temperature sensors and/or other control components, to provide greater controllability of the system for achieving more uniform thermal treatment across tissue or providing different thermal treatments to different portions of tissue. Thermally conducting elements integrated into the solid state devices and/or thermally coupled to one or more of the solid state devices of a solid state heating system may also be provided to distribute heat generated by the heating components to likewise achieve more uniform thermal treatment across tissue or provide different thermal treatments to different portions of tissue.

The solid state heating systems of the present disclosure may integrate or utilize one or more sensing elements such as temperature, pressure, proximity, optical absorption, reflectance, transmittance, Raman, or other types of sensors that measure characteristics of tissue and/or the system. These sensing elements may be integrated into the solid state devices or may be separate therefrom. For example, with respect to a surgical forceps, the solid state devices may be disposed within one of the jaw members, while one or more temperature sensors are disposed within on or the other jaw member to provide for better control of tissue heating by providing information on the rate at which heat is penetrating through tissue. Alternatively, solid state devices may be provided on both jaw members, with either or both including sensing elements.

The solid state devices or solid state heating systems of the present disclosure may be utilized, in addition to generating heat for thermally treating tissue, to provide control and/or power supply functionality. As an alternative to generating heat to heat tissue, the solid state devices or solid state heating systems may be utilized to minimize thermal gradients between tissue heating components and the rest of the medical device, e.g., via mounting the solid state devices or solid state heating systems on the opposite side(s) of the device relative to the tissue-contacting surface(s) thereof, thus allowing for maximum power delivery to tissue with decreased thermal load on the device.

The solid state heating systems of the present disclosure may utilize or incorporate heat-conducting elements to thermally connect the heat-generating transistors to tissue-contacting surface(s) of a device. Further, active or passive elements may be thermally connected to the heat-generating components or the tissue-contacting surface(s) of a device to provide cooling. Such elements may include heat sinks that are cooled (rapidly or slowly) by: being thermally coupled to the heating system, ambient air, cooling water, thermoelectric cooling elements, etc.

The heating systems of the present disclosure may be configured to provide suitable clearance within a device or portion thereof for other mechanical, electrical, or electromechanical components, mechanisms and/or systems. This may be accomplished by distributing one or more components of the heating system about the device, e.g., in one or more solid state devices or packages thereof, and/or distributing multiple solid state systems about the device. The distributed solid state devices and/or heating systems may be coupled to one another or may be independent of one another.

The present disclosure is further exemplified below with respect to particular devices and end effector assemblies, although the aspects and features of the presently-disclosed solid state heating systems are equally applicable for use with any suitable medical device.

Figure 1:
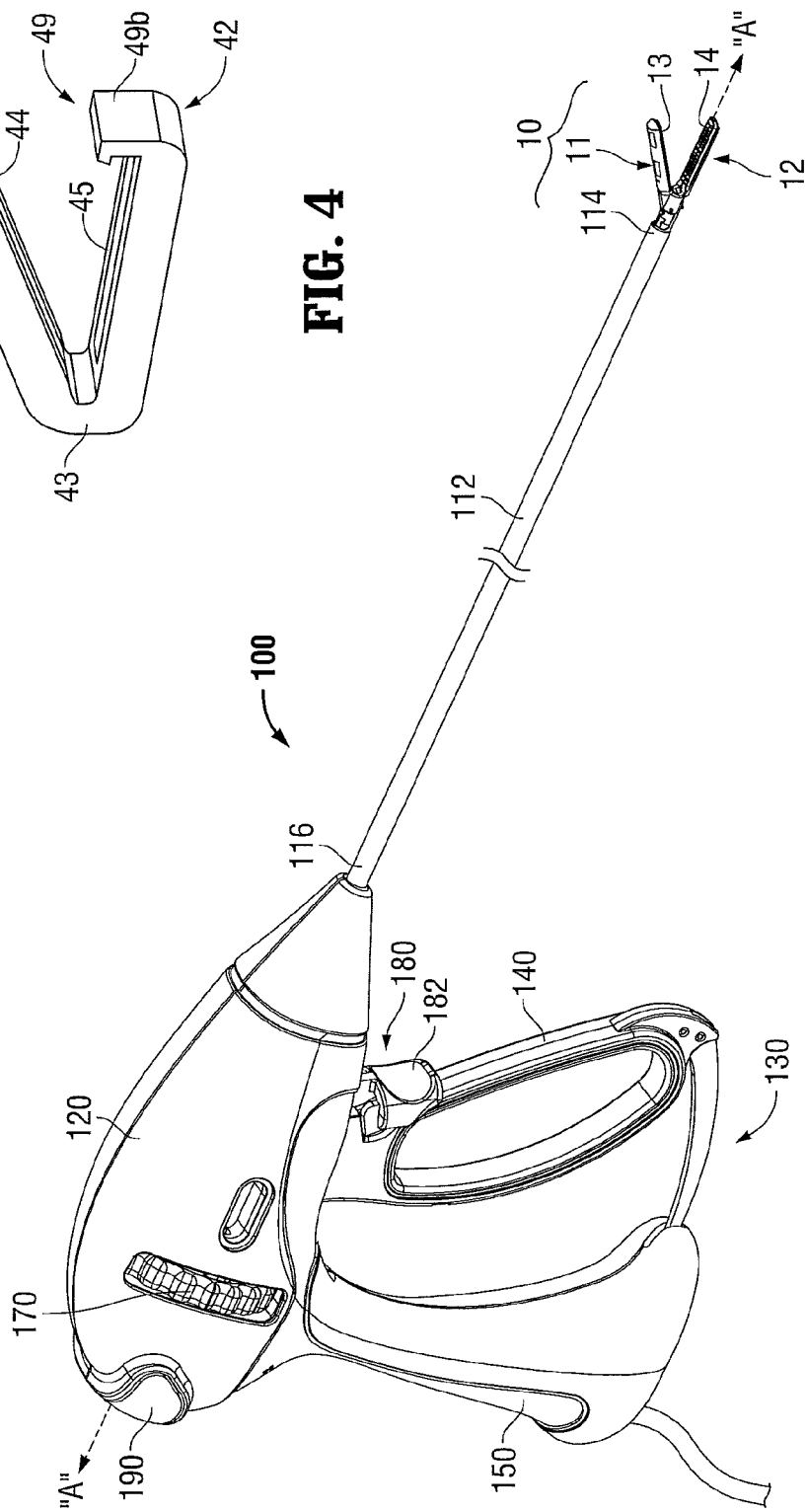
FIG. 1 is a front, perspective view of an endoscopic surgical forceps configured for use in accordance with the present disclosure.
Figure 2:
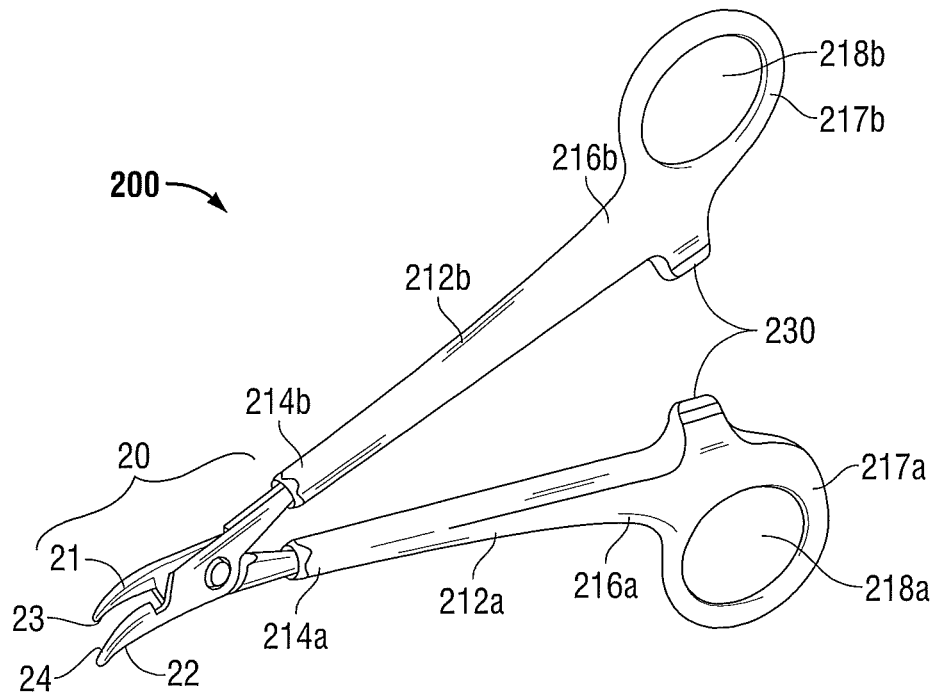
FIG. 2 is a front, perspective view of an open surgical forceps configured for use in accordance with the present disclosure.
Figure 3:
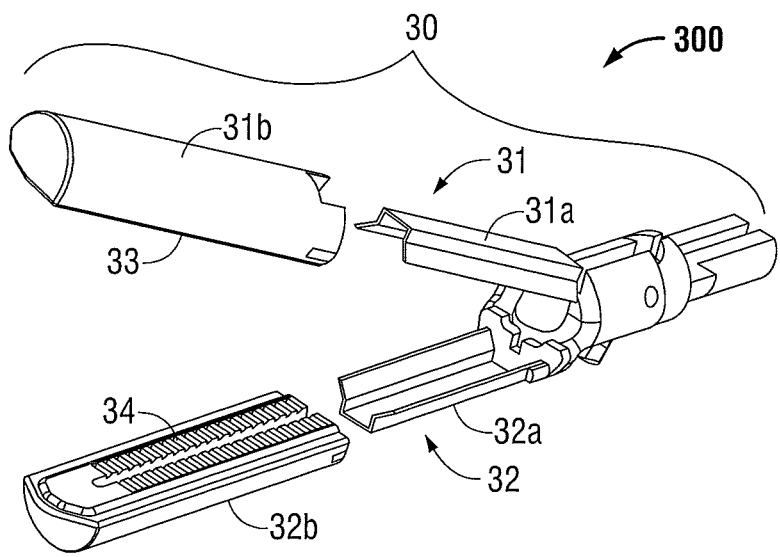
FIG. 3 is a front, perspective view of the distal end of a surgical forceps including reposable jaw members configured for use in accordance with the present disclosure.

Referring now to FIGS. 1-4, FIG. 1 depicts an endoscopic surgical forceps 100 for use in connection with endoscopic surgical procedures; FIG. 2 depicts an open surgical forceps 200 contemplated for use in connection with traditional open surgical procedures; FIG. 3 depicts a reposable forceps 300; and FIG. 4 depicts a tissue clip 400. For the purposes herein, either endoscopic forceps 100, open forceps 200, reposable forceps 300, tissue clip 400, or any other suitable medical device may be utilized in accordance with the present disclosure. Obviously, different electrical and mechanical connections and considerations apply to each particular type of device; however, the novel aspects of the present disclosure and the operating characteristics thereof remain generally consistent regardless of the configuration of the device used therewith.

Turning now to FIG. 1, endoscopic forceps 100 defines a longitudinal axis "A-A" and includes a housing 120, a handle assembly 130, a rotating assembly 170, a trigger assembly 180 and an end effector assembly 10. Forceps 100 further includes a shaft 112 having a distal end 114 configured to mechanically engage end effector assembly 10 and a proximal end 116 that mechanically engages housing 120. End effector assembly 10, as will be described in detail below, incorporates power, heat-generating, and control electronics therein for conductively heating tissue and controlling the heating of tissue to thermally treat tissue, thus obviating the need for supplying power, energy, and/or control signals to/from end effector assembly 10. As such, only end effector assembly 10 need include electrical components, while the remainder of forceps 100 may include only mechanical components, thus reducing the complexity of forceps 100. However, forceps 100 may also include one or more wires (not shown) extending through shaft 112 to connect end effector assembly 10 to activation button 190 of housing 120 for activating/deactivating the power, heat-generating, and/or control electronics. Alternatively or additionally, end effector assembly 10 may be coupled to control circuitry, an external display, and/or a remote power source, e.g., an external power source, or a power source contained in another part of forceps 100, for example, handle assembly 130.

With continued reference to FIG. 1, handle assembly 130 includes a fixed handle 150 and a movable handle 140. Fixed handle 150 is integrally associated with housing 120 and handle 140 is movable relative to fixed handle 150. Rotating assembly 170 is rotatable in either direction about a longitudinal axis "A-A" to rotate end effector 10 about longitudinal axis "A-A." Housing 120 houses the internal working components of forceps 100.

End effector assembly 10 is shown attached at distal end 114 of shaft 112 and includes a pair of opposing jaw members 11 and 12. One or both of the jaw members 11 and 12 includes a thermally-conductive tissue-contacting surface 13, 14, respectively, configured to conduct thermal energy to tissue grasped between jaw members 11, 12 to thermally treat, e.g., seal, tissue. End effector assembly 10 is designed as a unilateral assembly, i.e., where jaw member 12 is fixed relative to shaft 112 and jaw member 11 is movable relative to shaft 112 and fixed jaw member 12. However, end effector assembly 10 may alternatively be configured as a bilateral assembly, i.e., where both jaw member 11 and jaw member 12 are movable relative to one another and to shaft 112. In some embodiments, a knife assembly (not shown) is disposed within shaft 112 and a knife channel 615, 625 (FIG.

5B) is defined within one or both jaw members 11, 12 to permit reciprocation of a knife blade (not shown) therethrough, e.g., upon activation of trigger 182 of trigger assembly 180. The particular features of end effector assembly 10 will be described in greater detail hereinbelow.

Continuing with reference to FIG. 1, movable handle 140 of handle assembly 130 is ultimately connected to a drive assembly (not shown) that, together, mechanically cooperate to impart movement of jaw members 11 and 12 between a spaced-apart position and an approximated position to grasp tissue between tissue-contacting surfaces 13 and 14 of jaw members 11, 12, respectively. As shown in FIG. 1, movable handle 140 is initially spaced-apart from fixed handle 150 and, correspondingly, jaw members 11, 12 are disposed in the spaced-apart position. Movable handle 140 is depressible from this initial position to a depressed position corresponding to the approximated position of jaw members 11, 12.

Referring now to FIG. 2, open forceps 200 is shown including two elongated shafts 212a and 212b, each having a proximal end 216a and 216b, and a distal end 214a and 214b, respectively. Forceps 200 is configured for use with an end effector assembly 20 that is similar to end effector assembly 10 of forceps 100 (see FIG. 1). More specifically, end effector assembly 20 is attached to distal ends 214a and 214b of shafts 212a and 212b, respectively, and includes a pair of opposing jaw members 21 and 22 that are movable relative to one another. Each shaft 212a and 212b includes a handle 217a and 217b disposed at the proximal end 216a and 216b thereof. Each handle 217a and 217b defines a finger hole 218a and 218b therethrough for receiving a finger of the user. As can be appreciated, finger holes 218a and 218b facilitate movement of shafts 212a and 212b relative to one another from an open position, wherein jaw members 21 and 22 are disposed in spaced-apart relation relative to one another, to a closed position, wherein jaw members 21 and 22 cooperate to grasp tissue therebetween.

A ratchet 230 may be included for selectively locking jaw members 21 and 22 of forceps 200 relative to one another at various different positions. Ratchet 230 may include graduations or other visual markings that enable the user to easily and quickly ascertain and control the amount of closure force desired between the jaw members 21 and 22.

With continued reference to FIG. 2, end effector assembly 20, as will be described in detail below, incorporates power, heat-generating, and control electronics therein for conductively heating tissue grasped between jaw members 21, 22 to thermally treat, e.g., seal, tissue, thus obviating the need for supplying power, energy, and/or control signals to/from end effector assembly 20, although end effector assembly 20 of forceps 200 may additionally or alternatively be coupled to a remote power source (not shown), control circuitry (not shown), and/or an external display (not shown). One or both of the jaw members 21 and 22 further includes a thermally-conductive tissue-contacting surface 23, 24, respectively, configured to facilitate the conduction of thermal energy to tissue grasped between jaw members 21, 22 to treat, e.g., seal, tissue.

Similar to forceps 100 (FIG. 1), forceps 200 may further include a knife assembly (not shown) disposed within either of shafts 212a, 212b and a knife channel 615, 625 (FIG. 5B) defined within one or both jaw members 21, 22 to permit reciprocation of a knife blade (not shown) therethrough.

Turning now to FIG. 3, reposable forceps 300 may be configured as an open forceps, e.g., similar to forceps 200 (FIG. 2), an endoscopic forceps, e.g., similar to forceps 100 (FIG. 1), or in any other suitable configuration. Reposable forceps 300 includes an end effector assembly 30 similar to end effector assemblies 10, 20 (FIGS. 1, 2, respectively), except that jaw members 31, 32 each include a fixed jaw frame 31a, 32a and a removable jaw body 31b, 32b, respectively. Jaw bodies 31b, 32b are removably engagable with respective jaw frames 31a, 32a and incorporate power, heat-generating, and control electronics therein for conductively heating tissue to thermally treat, e.g., seal, tissue. As such, depending on a particular purpose, a pair of jaw bodies 31b, 32b having a particular configuration, e.g., including particularly configured power, heat-generating, and/or control electronics, may be selected and engaged to jaw frames 31a, 31b, respectively. This configuration not only provides for customization of forceps 300, but also obviates the need for supplying power, energy, and/or control signals to jaw bodies 31b, 32b. Further, this configuration, wherein the electrical components are fully disposed within jaw bodies 31b, 32b, allows the remainder of forceps 300 to include only mechanical components, thus reducing the complexity of forceps 300 and obviating the need for releasable electrical couplings between jaw bodies 31b, 32b and respective jaw frames 31a, 32a. Either or both of jaw bodies 31b, 32b further includes a thermally-conductive tissue-treating surface 33, 34, respectively, adapted to conduct heat to tissue grasped between jaw members 31, 32 to thermally treat, e.g., seal, tissue.

Referring now to FIG. 4, tissue clip 400 is an integrated or stand-alone end effector assembly including first and second jaw members 41, 42, respectively, coupled to one another by a flexible joint 43, although jaw members 41, 42 may alternatively be coupled to one another by a hinge, pivot, or any other suitable mechanism. Flexible joint 43 permits jaw members 41, 42 to move relative to one another between spaced-apart and approximated positions for grasping tissue therebetween. Jaw members 41, 42 of tissue clip 400 each further include a thermally-conductive tissue-contacting surface 44, 45, respectively. Power, heat-generating, and control electronics are disposed within either or both of jaw members 41, 42 for providing power to tissue clip 400, converting the power into thermal energy, and controlling the conduction of thermal energy to thermally-conductive tissue-contacting surfaces 44, 45 of jaw members 41, 42, respectively, to thermally treat, e.g., seal, tissue grasped between jaw members 41, 42. That is, tissue clip 400 is a fully integrated tissue-treating unit incorporating all the necessary mechanical and electrical components therein for conductively heating tissue to thermally treat tissue. A latch mechanism 49 including first and second latch components 49a, 49b disposed on first and second jaw members 41, 42, respectively, may also be provided for selectively locking jaw members 41 and 42 relative to one another in various different positions.

Figure 5A:
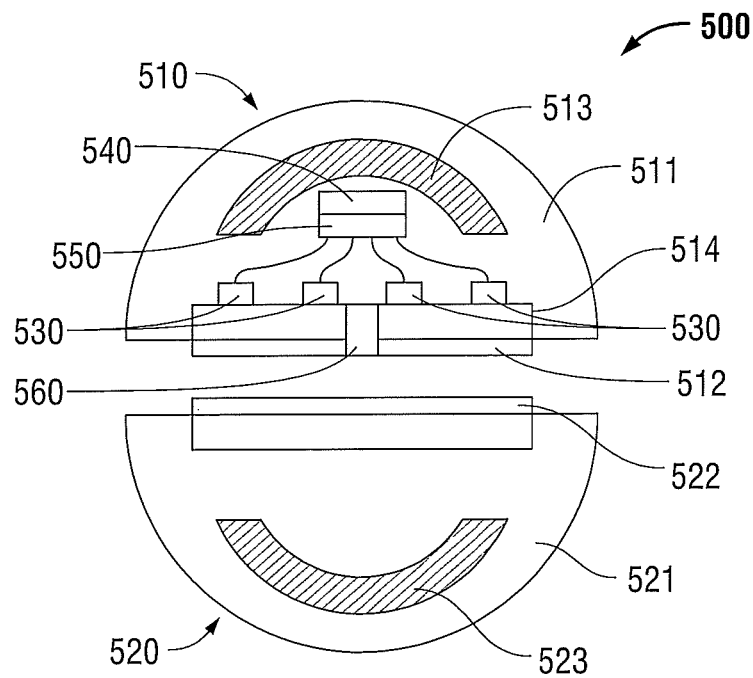
FIG. 5A is a transverse, cross-sectional view of an end effector assembly configured for use with any of the instruments of FIGS. 1-4.
Figure 5B:
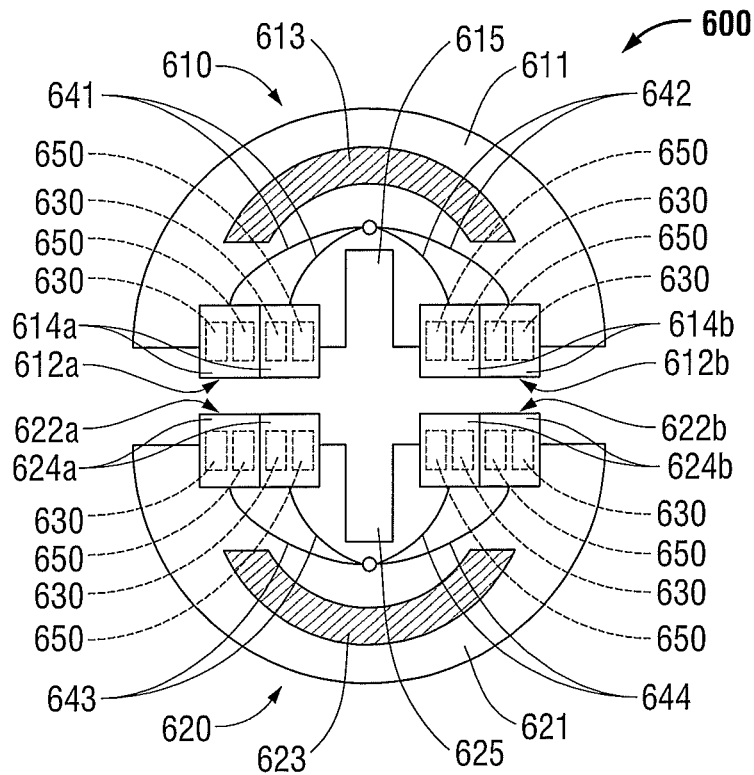
FIG. 5B is a transverse, cross-sectional view of another end effector assembly configured for use with any of the instruments of FIGS. 1-4.

Turning now to FIGS. 5A-5B, various embodiments of end effector assemblies 500, 600, configured for use with forceps 100 (FIG. 1), forceps 200 (FIG. 2), forceps 300 (FIG. 3), and/or tissue clip 400 (FIG. 4) are shown. Although shown as separate embodiments, any or of all of the features of end effector assemblies 500, 600, to the extent that they are consistent, may similarly be used in conjunction with the other end effector assembly 500, 600. Further any of the features detailed above may be incorporated into end effector assemblies 500, 600 in addition to or as an alternative to the features detailed below.

Continuing with general reference to FIGS. 5A-5B, each end effector assembly 500, 600 incorporate heat-generating systems and control systems. End effector assembly 500 further incorporates a power system, while end effector assembly 600 is configured to couple to a remotely disposed power system, e.g., exteriorly of the surgical instrument or in another portion of the surgical instrument such as, for example, the handle assembly. The heat-generating systems of end effector assemblies 500, 600 are formed from one or more solid state devices incorporated into, forming, packaged to define, or otherwise disposed in thermal communication with the tissue-contacting surface(s) of one or both of the jaw members thereof to facilitate conductive heating of tissue grasped between the jaw members to thermally treat, e.g., seal, tissue. The control systems may likewise be incorporated into one or more solid state devices, packaged together or separate from the heat-generating systems. As will be described in greater detail below, by incorporating the power system, heat-generating system, and/or control system into the end effector assembly and thermally coupling these systems to the tissue-contacting surfaces of the jaw members, the need for external power, heat-generating, and/or control electronics is obviated. Further, the use of a solid state heat-generating and/or control systems for conductive heating of tissue obviates the need to produce electrical energy, e.g., RF energy, microwave energy, etc., for transmission through tissue, thereby reducing the overall power requirements and complexity of the end effector assembly 500, 600. As such, sufficiently small power sources, e.g., batteries capable of being fully disposed within the end effector assembly 500, 600, miniature solid state heat-generating elements, e.g., transistor-based heating elements, and miniature solid state control elements, can be utilized.

With reference to FIG. 5A, end effector assembly 500 includes first and second jaw members 510, 520, respectively, each including a jaw housing 511, 521 and a thermally-conductive tissue-contacting surface 512, 522, respectively. Jaw housings 511, 521 are formed from insulative materials and are supported on a respective jaw frame 513, 523. Jaw frames 513, 523 are coupled to one another, e.g., via a pivot (not shown), to permit movement of jaw members 510, 520 relative to one another between a spaced-apart position and an approximated position for grasping tissue therebetween. Tissue-contacting surfaces 512, 522 are disposed on jaw housings 511, 521, respectively, and are configured to grasp tissue therebetween upon movement of jaw members 510, 520 to the approximated position. Either or both of the tissue-contacting surfaces, e.g., tissue-contacting surface 512, is thermally coupled to one or more solid state heat-generating elements 530 such that heat produced by heat-generating elements 530 may be conducted to tissue-contacting surface 512 (and/or tissue-contacting surface 522) for conductively heating tissue grasped between jaw members 510, 520 to thermally treat, e.g., seal, tissue. One example of a solid state, transistor-based heat-generating element 530 is described below (see FIG. 7), although other suitable solid state heat-generating elements 530 may also be provided as an alternative or in addition to transistor-based heating elements.

One of the jaw members, e.g., jaw member 510, may include a power source, e.g., a battery 540, disposed therein that is coupled to heat generating elements 530 for providing power to end effector assembly 500, e.g., for powering heat-generating elements 530. Further, one of the jaw members, e.g., jaw member 510, may include a control unit 550 disposed therein and coupled to either or both of heat-generating elements 530 and battery 540 for controlling heat-generating elements 530 and, thus, for controlling the heating of tissue grasped between jaw members 510, 520, as will be described in greater detail below. Control unit 550 may further be configured to control other components of the medical device associated with end effector assembly 500.

Continuing with reference to FIG. 5A, one or both of the jaw members, e.g., jaw member 510, further includes a substrate 514 disposed therein and positioned adjacent to and in thermal communication with the tissue-contacting surface 512 thereof. Substrate 514 incorporates, contains, mounts, supports, or otherwise couples to solid-state heat-generating elements 530 and/or solid state control unit 550. Substrate 514 may be the substrate upon which heat generating elements 530 and/or control unit 550 is formed, e.g., a silicon wafer. Alternatively or additionally, substrate 514 may be formed at least partially from a printed circuit board (PCB), a ceramic substrate, FR4 substrate, rigid plastic or composite substrate, flexible substrate (e.g., a flex circuit including polyimide, PEEK, polyester, PET, etc.), or any other suitable substrate or assembly that incorporates, mounts, receives or couples to heat-generating elements 530 and/or control unit 550. Substrate 514 may further be configured to facilitate the conduction or transfer of heat from the heat-generating elements 530 to tissue-contacting surface 512, e.g., substrate 514 may be formed from a thermally-conductive material in contact with tissue-contacting surface 512 or may otherwise be configured to facilitate thermal conduction between heat-generating elements 530 and tissue-contacting surface 512 (e.g., via wires, traces, other conductive elements, etc.). Substrate 514 may also define or incorporate the tissue-contact surface 512 therein or thereon and, in such embodiments, may further be configured to include any of the features detailed above. Insulative jaw housing 511 encapsulates substrate 514 such that substrate 514 is thermally coupled to tissue-contacting surface 512, but is otherwise surrounded by a thermally insulating material.

Battery 540 and/or control unit 550 may likewise be incorporated into, mounted, or otherwise coupled to substrate 514, similarly as detailed above with respect to heat-generating elements 530. More specifically, heat-generating elements 530, battery 540, and/or control unit 550 may be formed on substrate 514 as one or more solid state devices, e.g., integrated circuits (ICs) on a PCB, multi-chip modules (MCMs) packaged in a ceramic (or other suitable) substrate, System-in-Package (SiP) modules, a microprocessor, or other suitable electronics for generating heat to conductively heat tissue and control the heating of tissue.

Coupling battery 540, control unit 550, and/or heat-generating elements 530 together within one or more solid state devices on or in a substrate or package within end effector assembly 500 itself, e.g., without requiring external power or control electronics, facilitates customization for each particular procedure to be performed, which is particularly useful with respect to reposable forceps 300 (FIG. 3) and stand-alone tissue clips 400 (FIG. 4). Referring to FIG. 3, in addition to FIG. 5A, with regard to reposable forceps 300, rather than requiring an entirely new or different instrument customized for a particular procedure, all that is required is a new or different pair of jaw bodies 31b, 32b having a desired configuration of power, heat-generating, and/or control electronics. In other words, various different jaw bodies 31b, 32b may be provided for use with reposable forceps 300, each having a differently configured control unit and/or heat-generating element(s) to, for example, provide various different thermal treatment parameters and/or sealing algorithms. Accordingly, a generic reusable instrument configured to engage a desired set of jaw bodies 31b, 32b may be customized in accordance with the particular procedure to be performed. Further, when it is desired to update/upgrade the control unit 550, only new jaw bodies 31b, 32b are required, rather than an entirely new instrument. Jaw bodies 31b, 32b may also be configured for use with various different instruments, e.g., an endoscopic forceps similar to forceps 100 (FIG. 1) or an open forceps similar to forceps 200 (FIG. 2), depending on a particular purpose. Similarly with regard to tissue clips 400 (FIG. 4), various different tissue clips 400 (FIG. 4), each having a control unit and heat-generating element configured, e.g., having particular thermal treatment parameters and/or sealing algorithms, in accordance with a particular procedure, type/size of tissue, etc., may be provided. Exemplary control circuitry for incorporation into the control unit 550 of the various jaw bodies 31b, 32b and/or tissue clips 400 (FIG. 4) are described below.

In addition to facilitating customization, coupling control unit 550, and/or heat-generating elements 530 together within one or more solid state devices on or in a substrate or package allows for a minimal number of required external connections. For example, where battery 540 is not provided, such an integrated solid state device or device(s) in a package may require only three external connections: power, ground (return), and a control line for manually activating the device or manually terminating operation (see FIG. 5B). Where battery 540 is provided, only the control line may be required. The control line may further be configured to enable calibration, programming, synchronizing, updating, selecting different operating modes, etc.

With continued reference to FIG. 5A, control unit 550, as mentioned above, is coupled to battery 540 and/or heat-generating elements 530, or may include or be integrated with battery 540 and/or heat-generating elements 530 in one or more solid state devices, via packaging, or a substrate. Control unit 550 may include solid state or other components including, for example, logic or processing circuitry, e.g., microprocessors, field-programmable gate arrays (FPGAs), discrete logic circuits, etc.; timing circuitry; and/or other control circuitry for controlling, e.g., turning on/off, heat-generating elements 530 in accordance with one or more parameters, algorithms, or cycles. Further, control unit 550 may include or be coupled to one or more sensing elements 560, e.g., temperature sensors, pressure sensors, tissue property sensors, etc. Sensing element 560, as will be described in greater detail below, may be configured, for example, to sense the temperature and/or other properties of tissue grasped between jaw members 510, 520 such that control unit 550, in conjunction with sensing element 560, can control the thermal treatment of tissue via a feedback loop. Control unit 550, as mentioned above, may include one or more solid state devices, e.g., ICs, incorporated into substrate 514 or a package, or may assume any other suitable configuration, such as those mentioned above. The particular configuration of the control circuitry of the control unit 550 and/or the type and configuration of sensing elements 560 used therewith may be selected in accordance with the particular procedure to be performed, the type/size of tissue to be treated, and/or other factors. As mentioned above, various reposable jaw bodies 31b, 32b (FIG. 3) and/or various tissue clips 400 (FIG. 4) may be provided, each incorporating a differently configured control unit 550 adapted for use in a particular procedure (or procedures).

Referring to FIG. 5A in conjunction with FIG. 1, the use and operation of end effector assembly 500 in conjunction with forceps 100 is described. Although the use and operation of end effector assembly 500 is described with respect to forceps 100, end effector assembly 500 may be similarly configured for use with forceps 200, forceps 300, or tissue clip 400 (FIGS. 2, 3, and 4, respectively).

Initially, with jaw members 510, 520 disposed in the spaced-apart position, end effector assembly 500 is maneuvered into position such that tissue to be grasped and thermally treated, e.g., sealed, is disposed between jaw members 510, 520. Next, movable handle 140 is depressed, or pulled proximally relative to fixed handle 150 such that jaw member 510 is pivoted relative to jaw member 520 from the spaced-apart position to the approximated position to grasp tissue therebetween. More specifically, upon actuation of movable handle 150, a drive assembly (not shown) is activated such that a drive bar (not shown) is translated proximally through shaft 112, urging jaw member 510 to pivot relative to jaw member 520 from the spaced-apart position to the approximated position.

Once disposed in the approximated position grasping tissue between tissue-contacting surfaces 512, 522 of jaw members 510, 520, respectively, control unit 550 is activated, e.g., manually via depression of activation switch 190 of forceps 100 or automatically upon approximation of jaw members 510, 520 (or upon occurrence of some other condition) as determined by control unit 550 and sensing elements 560, such that power is supplied from battery 540 to heat-generating elements 530. Upon activation, e.g., upon supply of electrical power to heat-generating elements 530, heat-generating elements 530 produce heat that is conducted to tissue grasped between jaw members 510, 520 via substrate 514 and tissue-contacting surfaces 512, 514 to conductively heat tissue. Control unit 550, as mentioned above, and as will be described in greater detail below with reference to FIG. 8, may be configured to control the heating of tissue in conjunction with sensing elements 560 via feedback control, using a timing circuit, e.g., maintaining heat-generating elements 530 at a pre-determined temperature for a pre-determined time, or via any other suitable control mechanism to thermally treat tissue as desired.

With respect to tissue sealing in particular, the compression of tissue between jaw members 510, 520 brings tissue walls together and the conductive heating of tissue causes denaturizing and mixing of collagen and elastin to form an effective tissue seal. Heating of tissue to the target temperature for forming an effective tissue seal is dependent on a number of factors including the compressive force applied to tissue by jaw members 510, 520, the size and/or composition of tissue, the amount of thermal energy supplied to tissue, and other factors. Control unit 550 of end effector assembly 500 may thus be configured to control the heating of tissue in accordance with one or more of these factors, such that formation of an effective tissue seal (or otherwise effectively treating tissue) can be achieved. That is, control unit 550 and heat-generating elements 530 cooperate to start, regulate, and end the heating of tissue to facilitate formation of an effective tissue seal. Further, control unit 550 may be configured to individually and/or collectively control heat-generating elements 530 to achieve a more uniform tissue seal or other desired tissue effect. As can be appreciated, with respect to tissue heating for other purposes, the particular control settings and configuration of control unit 550 may be varied.

As mentioned above, control unit 550 may further include or may be coupled to one or more sensing elements 560 disposed on or along jaw member 510 (and/or jaw member 520) that are configured to automatically sense various properties of tissue or jaw members 510, 520 including, but not limited to: tissue type, tissue clarity, tissue compliance, tissue temperature, temperature of jaw members 510, 520, temperature of heat-generating elements 530, temperature of substrate 514, water content in tissue, opening angle of jaw members 510, 520, water motility in tissue, and/or jaw member closure pressure. Sensing elements 560 provide measurements to control unit 550, thus allowing control unit 550 to control heat-generating elements 530, e.g., to turn on/off one or more of heat generating elements 530, to heat tissue in accordance with the one or more properties of tissue and/or jaw members 510, 520 (and/or any of the components thereof) detected by sensing elements 560.

At the completion of tissue sealing, or other tissue treatment, a knife (not shown) may be advanced from shaft 112 of forceps 100 between jaw members 510, 520 to cut the previously-sealed tissue grasped therebetween, e.g., upon actuation of trigger 182 of trigger assembly 180. Alternatively, in embodiments where the configuration of the control unit 550 and heat-generating elements 530 so provides, e.g., wherein control unit 550 incorporates a thermal cutting algorithm or thermal cutting parameters, heat generating-elements 530 may be configured to conduct thermal energy to tissue to thermally dissect tissue along the previously-formed tissue seal. Thereafter, or in embodiments where tissue cutting is not desired, jaw members 510, 520 may be returned to the spaced-apart position to release the sealed and/or divided tissue, e.g., via moving movable handle 140 back to the initial position.

Referring now to FIG. 5B, another embodiment of an end effector assembly 600 configured for use with forceps 100 (FIG. 1), forceps 200 (FIG. 2), forceps 300 (FIG. 3), and/or tissue clip 400 (FIG. 4) is shown. End effector assembly 600 is similar to end effector assembly 500 (FIG. 5A) and may includes any of the features thereof, and vice versa. For purposes of brevity, only the differences between end effector assembly 600 and end effector assembly 500 (FIG. 5A) will be described in detail hereinbelow.

End effector assembly 600 includes first and second jaw members 610, 620, respectively, each including a jaw housing 611, 621 supported on a jaw frame 613, 623 and a pair of tissue-contacting surfaces 612a, 612b and 622a, 622b disposed on respective jaw housings 611, 621. One or both of jaw members 610, 620 is movable relative to the other between a spaced-apart position and an approximated position for grasping tissue therebetween. The tissue-contacting surfaces 612a, 612b and 622a, 622b of each jaw member 610, 620 are disposed on either side of a respective knife channel 615, 625 extending longitudinally through the respective jaw member 610, 620, and are configured to conduct heat to tissue grasped between jaw members 610, 620 to thermally treat, e.g., seal, tissue.

Continuing with reference to FIG. 5B, each jaw member 610, 620 includes a pair of packages 614a, 614b and 624a, 624b disposed on either side of knife channels 615, 625, respectively, that define the respective tissue-contacting surfaces 612a, 612b and 622a, 622b of jaw members 610, 620. As an alternative to packages 614a, 614b and 624a, 624b, substrates defining tissue-contacting surfaces 612a, 612b and 622a, 622b may alternatively be provided.

Each package 614a, 614b and 624a, 624b incorporates one or more solid state heat-generating elements 630 and one or more solid state control units 650 for controlling the respective heat-generating elements 630. Packages 614a, 614b and 624a, 624b are coupled to an external power source (not explicitly shown) via wires 641, 642 and 643, 644, respectively. Sensing elements (not explicitly shown) may also be provided for use in conjunction with one or more of packages 614a, 614b, 624a, 624b. The heat-generating element(s) 630 corresponding to each package 614a, 614b and 624a, 624b may be independently or collectively operated to achieve a desired tissue effect.

Figure 6:
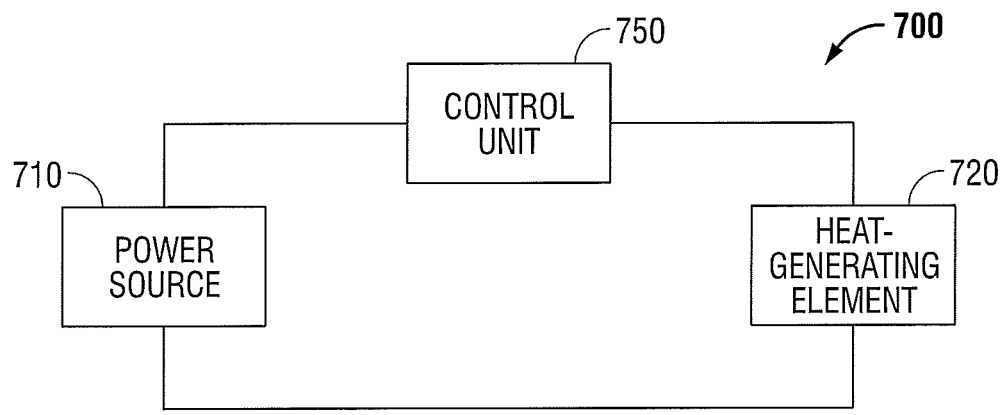
FIG. 6 is a schematic illustration of power, heating, and control electronics configured for use with any of the end effector assemblies of FIGS. 5A-5B.
Figure 7:
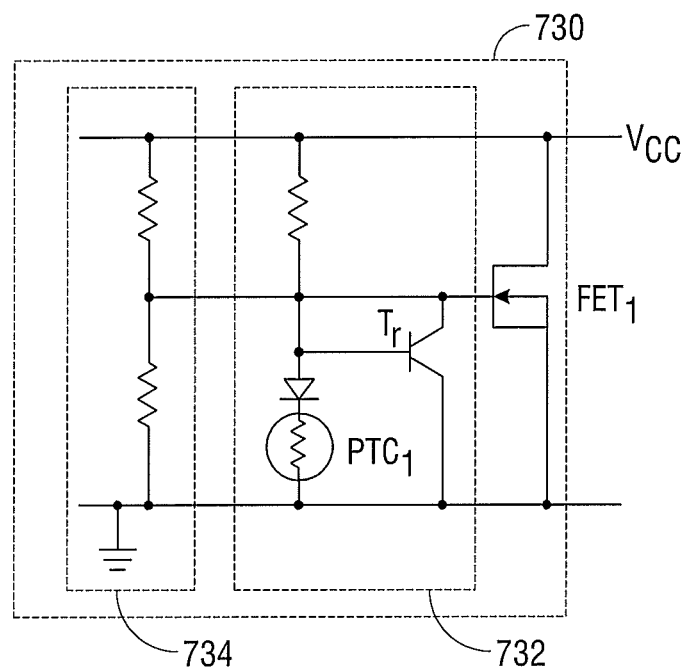
FIG. 7 is a schematic diagram of a heating circuit configured for use with any of the end effector assemblies of FIGS. 5A-5B.
Figure 8:
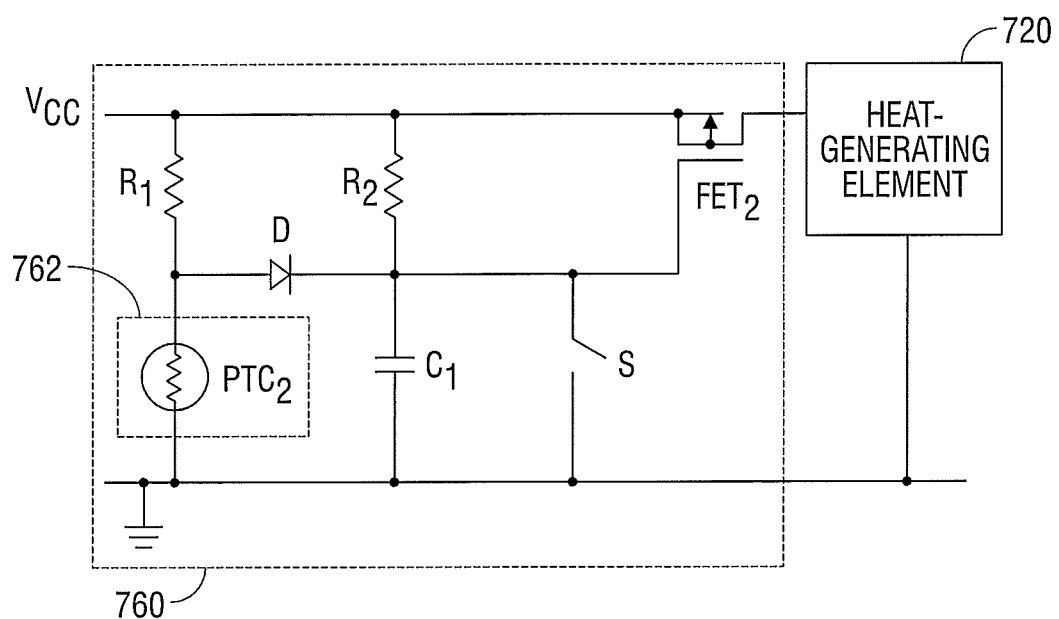
FIG. 8 is a schematic diagram of a control circuit configured for use with any of the end effector assemblies of FIGS. 5A-5B.

Turning now to FIGS. 6-8, and with initial reference to FIG. 6, schematics of an electronics system 700, e.g., the power source 710, the heat-generating element 720, and the control unit 750, configured for use with end effector assemblies 500, 600 (FIGS. 5A-5B, respectively), or any other suitable end effector assembly, are shown and described. As shown in FIG. 6, and as mentioned above, the electronics system 700 of each end effector assembly generally incorporates a power source 710, e.g., a battery, one or more heat-generating elements 720, and a control unit 750 that are coupled to one another (in any suitable configuration, such as those detailed above) to conductively heat and control the heating of tissue to achieve a desired tissue effect, e.g., to seal tissue.

Turning now to FIG. 7, in conjunction with FIG. 6, one embodiment of a heat-generating circuit 730 for the heat-generating element 720 is shown configured as a constant-temperature heat source. Heat-generating circuit 730 is formed as a transistor-based, solid state heating device configured to receive power from power source 710 and to produce heat for conduction to tissue to thermally treat tissue. More specifically, heat-generating circuit 730 includes a power supply $V_{cc}$ that is coupled to power source 710 for receiving power therefrom, a power-dissipating, e.g., heat-producing, Field-Effect Transistor (FET) $FET_1$, e.g., a Metal-Oxide-Semiconductor Field-Effect transistor (MOSFET) or a junction gate field-effect transistor (JFET), a temperature-control circuit 732, and a biasing circuit 734. The biasing circuit 734 is configured to operate $FET_1$ in a highly dissipating manner to produce heat for conductively heating tissue. The temperature-control circuit 732 includes a positive temperature coefficient thermistor $PTC_1$ thermally coupled to $FET_1$ for substantially maintaining $FET_1$ at a constant temperature. That is, as $FET_1$ heats up, $PTC_1$ likewise heats up, thereby increasing in resistance and reducing the drive to $FET_1$ by switching ON the transistor Tr. When the $FET_1$ cools down, $PTC_1$ likewise cools down and its resistance decreases such that the drive to $FET_1$ is increased by switching OFF the transistor Tr. Thus, $FET_1$ can be heated to and maintained at a substantially constant temperature, or within a sufficiently narrow temperature range.

Turning now to FIG. 8, in conjunction with FIGS. 6 and 7, one embodiment of a solid state-implemented control circuit 760 for the control unit 750 is shown configured for electrical coupling between the power source 710 and heat-generating element 720 for controlling, e.g., turning ON/OFF, the supply of electrical energy to heat-generating element 720. Control circuit 760 is configured as an analog timing circuit for heating tissue to a pre-determined temperature for a pre-determined amount of time, although other suitable control circuits are also contemplated utilizing either analog or digital methods. More specifically, control circuit 760 includes a sensing element 762 (similar to sensing element 560 (FIG. 5A), above), e.g., a PTC thermistor $PTC_2$, configured to sense the temperature of tissue to be thermally treated, and a FET $FET_2$ that is coupled between power source 710 and heat-generating element 720 for turning ON/OFF the supply of power to heat-generating element 720 such that tissue in thermal contact with temperature-sensing element 762 can be heated to a target temperature and maintained at or above that target temperature for a pre-determined amount of time to facilitate thermal tissue treatment, e.g., tissue sealing.

In one implementation, control circuit 760 may be used with a constant-temperature heat-generating element 720, although control circuit 760 may also be used with other suitable heat-generating elements 720. With regard to constant temperature heat-generating element 720, temperature-sensing element 762 may be positioned on or in the jaw member opposing the jaw member containing heat-generating element 720. In this configuration, upon activation of heat-generating element 720, tissue contacting the jaw member containing heat-generating element 720 is heated relatively quickly to and is maintained at the predetermined "constant" temperature. Heat-generating element 720 is maintained at this predetermined "constant" temperature until temperature-sensing element 762, which is disposed on or in the opposing jaw member, has been sufficiently heated, indicating that tissue adjacent temperature-sensing element 762 has been sufficiently heated. When sufficiently heated, indicating the end the heating cycle, control circuit 760 operates to turn OFF the supply of power to heat-generating element 720.

More specifically, in use, momentary contact switch S is used to zero the voltage across capacitor C, turning on $FET_2$, and initiating heating by heat-generating element 720. Capacitor C charges very slowly through resistor $R_2$, which defines an upper bound on the duration of the heating cycle. As temperature-sensing element 762 is heated, its resistance increases, raising the voltage of the node between it and resistor $R_1$ and eventually allowing capacitor C to be charged through diode D with a time constant determined by the capacitance and the resistance of the voltage divider formed by $R_1$ and temperature-sensing element 762. This rate is typically much faster than the charging of capacitor C via $R_2$. The increasing voltage across capacitor C eventually turns off $FET_2$, ending the heating cycle.

Put more generally, timing circuit 760 is activated (and the charging of capacitor C begins) once tissue to be thermally treated reaches the target temperature, as sensed by sensing element 762. Capacitor C is charged to equilibrium (over a pre-determined amount of time), at which point $FET_2$ is switched OFF to cut off the supply of power to heat-generating element 720. That is, timing circuit 760 turns OFF heat-generating element 720 once tissue has been heated to the target temperature for a pre-determined amount of time. Thermistor $PTC_2$, resistors $R_1$, $R_2$, and capacitor C may be configured in accordance with a desired target temperature and "on time" of the control circuit 760. The target temperature and "on time" may depend on the particular procedure to be performed, the type/size of tissue to be thermally treated and/or other factors. As mentioned above, various different jaw bodies 31b, 32b of a reposable forceps 300 (see FIG. 3) and/or various different tissue clips 400 (FIG. 4) may be provided, each configured for a particular procedure (or procedures), e.g., each incorporating a control circuit 760 having a target temperature and "on time" adapted for a particular procedure (or procedures).

Momentary contact switch S, which, as mentioned above, is used to zero the voltage across capacitor C, turn on $FET_2$, and initiate heating by heat-generating element 720, may be coupled to activation switch 190 (FIG. 1) of forceps 100 for manually controlling the initiation of the heating cycle upon activation of activation switch 190, while completion of the heating cycle, e.g., once tissue has been heated to the target temperature for the pre-determined amount of time, is automatically controlled via control circuit 760.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A medical device for treating tissue, comprising:
an end effector assembly including first and second jaw members, at least one of the jaw members movable relative to the other between a spaced-apart position and an approximated position for grasping tissue therebetween, at least one of the jaw members including:
a jaw housing; and
an integrated circuit package disposed on the jaw housing and defining a tissue-contacting surface thereof, the integrated circuit package including:
a solid state heating element including at least one transistor configured to generate heat to thermally treat tissue;
a battery configured to supply energy to the at least one transistor of the solid state heating element such that the at least one transistor generates heat to thermally treat tissue; and
control circuitry configured to regulate the supply of energy from the battery to the at least one transistor to thereby regulate heat generation by the solid state heating element.

2. The medical device according to claim 1, further comprising at least one temperature-sensing element configured to sense a temperature of at least one of: the solid state heating element, tissue, and another element thermally coupled to the solid state heating element or tissue.

3. The medical device according to claim 2, wherein the control circuitry is coupled to the temperature-sensing element for feedback-based control of the supply of energy from the battery to the at least one transistor.

4. The medical device according to claim 2, wherein the solid state heating element is disposed within one of the jaw members and wherein the temperature-sensing element is disposed within the other of the jaw members.

* * * * *